(12) United States Patent
Bhatt et al.

(10) Patent No.: US 7,261,466 B2
(45) Date of Patent: *Aug. 28, 2007

(54) IMAGING INSPECTION APPARATUS WITH DIRECTIONAL COOLING

(75) Inventors: Ashwinkumar C. Bhatt, Endicott, NY (US); Varaprasad V. Calmidi, Binghamton, NY (US); James J. McNamara, Jr., Vestal, NY (US); Sanjeev Sathe, San Jose, CA (US)

(73) Assignee: Endicott Interconnect Technologies, Inc., Endicott, NY (US)

( * ) Notice: Subject to any disclaimer, the term of this patent is extended or adjusted under 35 U.S.C. 154(b) by 267 days.

This patent is subject to a terminal disclaimer.

(21) Appl. No.: 11/141,349

(22) Filed: Jun. 1, 2005

(65) Prior Publication Data
US 2007/0009084 A1    Jan. 11, 2007

(51) Int. Cl.
*H01J 35/12* (2006.01)
*G01N 23/04* (2006.01)

(52) U.S. Cl. .................... 378/199; 378/57
(58) Field of Classification Search ............. 378/57, 378/130, 141, 199, 200; 209/589; 250/358.1, 250/359.1
See application file for complete search history.

(56) References Cited

U.S. PATENT DOCUMENTS

| | | | |
|---|---|---|---|
| 4,020,346 A * | 4/1977 | Dennis ................... | 378/57 |
| 5,020,086 A | 5/1991 | Peugeot | |
| 5,026,983 A | 6/1991 | Meyn | |
| 5,259,012 A | 11/1993 | Baker et al. | |
| 5,367,552 A | 11/1994 | Peschmann | |
| 5,483,569 A | 1/1996 | Annis | |
| 5,524,133 A | 6/1996 | Neale et al. | |
| 5,583,904 A | 12/1996 | Adams | |
| 5,629,966 A | 5/1997 | Dykster et al. | |
| 5,991,358 A | 11/1999 | Dolazza et al. | |
| 6,018,562 A | 1/2000 | Willson | |
| 6,052,433 A | 4/2000 | Chao | |
| 6,236,709 B1 | 5/2001 | Perry et al. | |
| 6,400,799 B1 | 6/2002 | Andrews | |
| 6,419,389 B1 * | 7/2002 | Fuchs et al. ............. | 378/199 |
| 6,496,564 B2 | 12/2002 | Price et al. | |
| 6,529,579 B1 | 3/2003 | Richardson | |
| 6,619,841 B2 | 9/2003 | Lenz | |
| 6,669,366 B2 | 12/2003 | Busse et al. | |
| 6,708,814 B2 * | 3/2004 | Wagstaffe ................ | 198/632 |
| 6,709,156 B1 | 3/2004 | Hell et al. | |
| 6,714,626 B1 | 3/2004 | Subraya et al. | |
| 6,778,635 B1 | 8/2004 | Richardson | |
| 6,963,632 B2 * | 11/2005 | Kendall .................. | 378/141 |

\* cited by examiner

*Primary Examiner*—Edward J. Glick
*Assistant Examiner*—Irakli Kiknadze
(74) *Attorney, Agent, or Firm*—Hinman, Howard & Kattell, LLP; Lawrence R. Fraley

(57) ABSTRACT

An imaging inspection apparatus which utilizes a plurality of individual imaging devices (e.g., X-ray Computer Tomography scanning devices) for directing beams onto articles having objects therein to detect the objects based on established criteria. The apparatus utilizes a cooling structure for directing cooling fluid (e.g., air) toward and over the devices, the structure including a fan for directing cooling fluid in a first direction and a plurality of fluid deflectors for deflecting at least part of the fluid toward respective ones of the devices.

20 Claims, 6 Drawing Sheets

IMAGING INSPECTION APPARATUS WITH DIRECTIONAL COOLING

CROSS REFERENCE TO CO-PENDING APPLICATIONS

In Ser. No. 11/091,521, entitled "IMAGING INSPECTION APPARATUS", filed Mar. 29, 2005, there is defined an imaging inspection apparatus which utilizes a plurality of individual imaging inspection devices (e.g., X-ray Computer Tomography scanning devices) positioned on a frame for directing beams onto articles having objects therein to detect the objects based on established criteria. Among other features, the apparatus utilizes a conveyor which is not physically coupled to the frame having the imaging inspection devices to pass the articles along a path of travel to an inspection location within the apparatus, whereupon the inspection devices direct beams onto the article and the beams are detected and output signals provided to a processing and analysis assembly which analyzes the signals and identifies certain objects which meet the criteria. Ser. No. 11/091,521 is now U.S. Pat. No. 7,177,391, having issued Feb. 13, 2007.

In Ser. No. 11/141/494, entitled "IMAGING INSPECTION APPARATUS WITH IMPROVED COOLING", filed Jun. 1, 2005, there is defined an imaging inspection apparatus in which cooling fluid (e.g., liquid refrigerant) is forced (e.g., pumped) through passages within the frame structure of the apparatus immediately adjacent the heat-generating imaging devices. A heat exchanger is used to cool the fluid after passing near the devices, such that the fluid can be re-circulated through the frame structure.

Both of the above pending applications are assigned to the same Assignee as the present invention.

TECHNICAL FIELD

The invention relates to inspection apparatus designed for inspecting articles such as luggage, baggage, mail, etc. More particularly, the invention relates to such apparatus which utilize X-ray imaging and the like.

BACKGROUND OF THE INVENTION

The use of imaging inspection apparatus of the above type is known, including those which utilize X-ray imaging. Such apparatus are used to inspect articles such as personal luggage of airplane travelers at airports for such undesirable items as explosives and drugs. One particularly successful example of such apparatus is that which utilizes what is referred to in the art as "X-ray Computer Tomography" (hereinafter also referred to as, simply, XCT). XCT apparatus are in wide use in the medical field for providing medical imaging such as patient body X-rays. XCT (often referred to in the medical profession simply as "CT scanning") produces a cross sectional image from a grouping of attenuation measurements taken at different angles about an object such as a patient's chest or head, while the patient is maintained in a stationary position.

Some versions of the above apparatus have been modified to be more adaptable to taking images for non-medical purposes. In U.S. Pat. No. 5,367,552, issued Nov. 22, 1994, for example, a rotating XCT scanning unit is used which requires an object to remain stationary during scanning. This apparatus is designed for detecting concealed objects, such as explosives, drugs, or other contraband in a person's luggage. The apparatus uses scanning to identify concealed objects with a density corresponding to the density of target objects such as explosives or drugs. To reduce the amount of scanning required, a number of pre-scanning approaches are described in this patent. Based upon pre-scan data, selected locations for scanning are identified. The resulting scan data is utilized to automatically identify objects of interest, which identification is further verified through automatic analysis of such attributes as shape, texture, context, and X-ray diffraction. The objects of interest are then reconstructed and displayed on a computer monitor for visual analysis by the apparatus operator.

High speed scanning, such as that useful for scanning luggage of large numbers of travelers in a relatively shorter time period than provided by conventional stationary apparatus, requires that even further modifications be made. One such apparatus is described in U.S. Pat. No. 6,236,709, issued May 22, 2001, in which a continuous, XCT imaging system includes a conveyor which moves a closed package for being scanned along the conveyor past three spaced sensing stations. At each sensing station a plurality of X-ray sources each emit a fan beam in the same scan plane which passes through the package to a plurality of detectors opposite the X-ray sources. One scan is a vertical perpendicular scan plane relative to the direction of travel of the package along the conveyor belt and the remaining two scan planes are horizontal scan planes at right angles and transverse to the direction of travel. One horizontal scan plane is a left to right scan plane while the remaining scan plane is a right to left scan plane. Each detector provides multiple energy outputs for the same data point in a scan slice, and the detector outputs are stored until all three sensing stations have scanned the same cross sectional view of the package in three directions. Scans are sequentially taken as the package moves continuously through the sensing stations and scanned data corresponding to cross sectional views of the package is accumulated. The stored data is calibrated and normalized and then used in a Computer Tomographic algebraic reconstruction technique. This is described in this patent as a "multi-spectral CT reconstruction", where the density of a reconstructed object is determined by the attenuation which it causes in the scanning X-rays while the atomic number of the object is determined from the multiple energy scan output. In a classifier, the density and atomic number are compared to a table containing density and atomic number identification values for specific objects to be located.

Accurate, rapid inspection of moving articles such as multiple luggage pieces, often having many different sizes and shapes, is, understandably, a relatively difficult task, as indicated by just some of the difficulties mentioned in some of the patents cited herein and elsewhere in the literature pertaining to this art with respect to articles in both stationary and moving positions. When utilizing many heat-generating devices such as X-ray sources, it is essential that these sources operate at the proper temperature. Otherwise, the devices may be subject to failure, which is costly in both replacement terms as well as apparatus shutdown. Maintaining these heat-generating devices at proper temperature is thus critical to assuring effective apparatus operation.

Attention is directed to the following U.S. Patents which describe various types of scanning apparatus (in addition to those cited in the patents above), some of which utilize some form of means to provide cooling for the apparatus.

In U.S. Pat. No. 6,778,635, issued Aug. 17, 2004, there is described an x-ray tube cooling system which utilizes a heat sink partially disposed within an evacuated housing of the x-ray tube and having a cooling block partially received within the bearing housing to absorb heat transmitted to the bearing assembly and bearing housing. Extended surfaces are disposed in a coolant chamber defined by the cooling block and a shell within which the cooling block is partially received. The shell defines a coolant chamber entrance and coolant chamber exit in fluid communication with the coolant chamber. The coolant chamber entrance and exit communicate with corresponding coolant inlet and outlet passageways, respectively, cooperatively defined by a pair of insulators which retain the heat sink in a predetermined orientation within an evacuated envelope of an x-ray device. A circulating coolant contacts the extended surfaces and thereby removes heat from various structures of the x-ray device.

In U.S. Pat. No. 6,714,626, issued Mar. 30, 2004, there is described an x-ray tube cooling assembly which includes an electron collector body coupled to an x-ray tube window and having a first coolant circuit. The coolant circuit includes a coolant inlet and a coolant outlet. The coolant outlet directs coolant at an x-ray tube window surface to impinge upon and cool the x-ray tube window. The coolant is reflected off the reflection surface to impinge upon and cool the x-ray tube window.

In U.S. Pat. No. 6,709,156, issued Mar. 23, 2004, there is described a cooling device for an X-ray source that is arranged in a gantry around a rotational axis. The device includes a ring-like heat exchanger that is positioned at the gantry and is thermally connected to the X-ray source. The cooling device is useable in a computed tomography apparatus having the X-ray source.

In U.S. Pat. No. 6,669,366, issued Dec. 30, 2003, there is described an X-ray examination apparatus in which the X-ray detector and the X-ray source are subject to keeping the temperature constant and to cooling by way of a common cooling "circuit". A cooling medium of constant temperature is applied to the X-ray detector in order to make the detector operate at desired temperatures. The temperature of the cooling medium, increased a first time, allegedly performs cooling of the X-ray source. The heated cooling medium, after application to the X-ray detector, is applied to the X-ray source where a second exchange of heat takes place, so the X-ray source is cooled without utilizing an additional cooling circuit.

In U.S. Pat. No. 6,619,841, issued Sep. 16, 2003, there is described a fluid-cooled X-ray tube which includes a closed coolant "circuit" in which coolant circulates for the elimination of generated heat. In order to improve the cooling capacity, micro-capsules containing a phase-change material (PCM) are added to the coolant. In this arrangement, heat arising from the X-ray tube is intermediately stored in the PCM storage elements for a certain time span. Dependent on the selected material of the PCM and the amount of the PCM storage elements introduced into the coolant, the temperature of the coolant can be kept nearly constant over a specific time segment despite the heat arising from the tube during X-ray generation. Compared to conventional measures for cooling an X-ray tube, this patent mentions that the rise in temperature of the coolant is retarded by this arrangement, so that the X-ray radiator can be more highly stressed (loaded) over the same operating duration, or the operating duration of the X-radiator can be significantly lengthened given the same load. Described PCM materials for this purpose are paraffins whose melting temperatures lie between ninety and one hundred and twelve degrees Celsius. Mentioned alternatives to paraffin include fatty alcohols, fatty acids, hydrates of sodium carbonate, sodium acetate, calcium chloride and lithium magnesium nitrate.

In U.S. Pat. No. 6,529,579, issued Mar. 4, 2003, there is described a cooling system for high-powered X-ray tubes. The cooling system includes a reservoir containing liquid coolant, in which the high-powered X-ray tube is partially immersed. In general, the liquid coolant is cooled and then circulated through the reservoir by an external cooling unit. The cooling system also includes a shield structure attached to the vacuum enclosure of the X-ray tube and disposed substantially about the aperture portion of the vacuum enclosure, thereby defining a flow passage proximate the aperture portion. Liquid coolant supplied by the external cooling unit enters the flow passage by way of an inlet port in the shield structure. After passing through the flow passage and transferring heat out of the aperture portion, the liquid coolant is discharged through an outlet port in the shield structure and enters the reservoir to repeat the cycle.

In U.S. Pat. No. 6,496,564, issued Dec. 17, 2002, there is described an X-ray system with an X-ray "generating device" which includes an X-ray tube mounted in a casing holding a circulating, cooling medium. According to the description, the X-ray generating device includes a support mechanism mounted within the X-ray generating device in a manner for adjustably positioning, relative to the casing, the focal spot alignment path of generated X-rays. Additionally, the device includes a cooling mechanism having an inlet chamber for channeling the cooling medium within the support mechanism. Still further, a cooling stem may be positioned within the inlet chamber to increase the heat exchange surface area exposed to the cooling medium.

In U.S. Pat. No. 6,400,799, issued Jun. 4, 2002, there is described an x-ray tube cooling system which utilizes a shield structure connected between a cathode cylinder and an x-ray tube housing and disposed between the electron source and the target anode. The system uses a plurality of cooling fins to improve overall cooling of the x-ray tube and the shield so as to extend the life of the x-ray tube and related components. When immersed in a reservoir of coolant fluid, the fins facilitate improved heat transfer by convection from the shield to the to the coolant fluid. The cooling effect achieved with the cooling fins is further augmented by a convective cooling system provided by a plurality of passageways formed within the shield, which are used to provide a fluid path to the coolant. In particular, a cooling unit takes fluid from the reservoir, cools the fluid, and then circulates the cooled fluid through cooling passages. The coolant is then output from the passageway and directed over the cooling fins. In some embodiments, the passageways are oriented so as to provide a greater heat transfer rate in certain sections of the shield than in other sections.

U.S. Pat. No. 6,052,433, issued Apr. 18, 2000, describes an apparatus for performing dual-energy X-ray imaging using two-dimensional detectors. The apparatus consists of an X-ray source, a 2-dimensional X-ray detector, a beam selector, and a second 2-dimensional X-ray detector. The subject is located between the X-ray source and first detector. The beam selector prevents primary X-rays from reaching selected locations of the second (rear) detector. A pair of primary dual-energy images is obtained at the rear detector. Using a dual-energy data decomposition method, a low-resolution primary X-ray first detector image is calculated, from which a high-resolution primary dual-energy image pair is calculated. In addition, the data decomposition method is used to calculate a pair of high-spatial-resolution material composition images.

U.S. Pat. No. 6,018,562, issued Jan. 25, 2000, describes an apparatus for automatic recognition and identification of concealed objects and features thereof, such as contraband in baggage or defects in articles of manufacture. The apparatus uses multiple energy X-ray scanning to identify targets having a spectral response corresponding to a known response of targets of interest. Detection sensitivity for both automatic detection and manual inspection are improved through the multiple-energy, multi-spectral technique. Multi-channel processing is used to achieve high throughput capability. Target identification may be verified through further analysis of such attributes as shape, texture, and context of the scan data. The apparatus uses a statistical analysis to predict the confidence level of a particular target identification. A radiograph, CT image, or both may be reconstructed and displayed on a computer monitor for visual analysis by the apparatus operator. Finally, the apparatus may receive and store input from the operator for use in subsequent target identification.

U.S. Pat. No. 5,991,358, issued Nov. 23, 1999, describes a data acquisition system for use in a CT scanner which consists of an analog-to-digital converter for generating digital signals in response to analog signals representative of projection data taken at a relatively constant sampling rate. The apparatus also uses an interpolation filter for generating projection data for a plurality of predetermined projection angles as a function of the digital signals irrespective of the sampling rate. This patent references a known system which includes an array of individual detectors disposed as a single row in the shape of an arc of a circle having a center of curvature at a certain point, referred to as the "focal spot", where the radiation emanates from the X-ray source. The X-ray source and the array of detectors in this known system are positioned so that the X-ray paths between the source and each of the detectors all lie in the same plane (hereinafter the "rotation plane" or "scanning plane") which is normal to the rotation axis of the disk. Since the X-ray paths originate from what is substantially a point source and extend at different angles to the detectors, the X-ray paths form a "fan beam." The X-rays incident on a single detector at a measuring interval during a scan are commonly referred to as a "ray", and each detector generates an analog output signal indicative of the intensity of its corresponding ray. Since each ray is partially attenuated by all the mass in its path, the analog output signal generated by each detector is representative of an integral of the density of all the mass disposed between that detector and the X-ray source (i.e., the density of the mass lying in the detector's corresponding ray path) for that measuring interval.

U.S. Pat. No. 5,629,966, issued May 13, 1997, describes a real time radiographic test system which consists of a protective housing and a conveyor for conveying articles to be tested through the housing. A real time radiographic test instrument is located in the housing for performing a real time radiographic test on the article. The test instrument includes X-ray equipment disposed for directing an X-ray beam within the housing in a direction which does not intersect the conveyor. An article-handling actuator is located in the housing for repositioning an article from the conveyor to a position in registry with the X-ray beam, for maintaining the article in registry with the X-ray beam while the real time radiographic test is performed on the article and thereafter returning the article to the conveyor. The article-handling actuator and the X-ray equipment are designed such that each article to be tested is positioned substantially identically relative to the X-ray beam.

U.S. Pat. No. 5,583,904, issued Dec. 10, 1996, describes a laminographic system that allows generation of high speed and high resolution X-ray laminographs by using a continuous scan method with two or more linear detectors and one or more collimated X-ray sources. Discrete X-ray images, with different viewing angles, are generated by each detector. The discrete X-ray images are then combined by a computer to generate laminographic images of different planes in the object under test, or analyzed in such a manner to derive useful data about the object under test. This system does not require any motion of the source or detectors, but simply a coordinated linear motion of the object under test. Higher speed is achieved over conventional laminography systems due to the continuous nature of the scan, and due to the ability to generate any plane of data in the object under test without having to re-image the object.

U.S. Pat. No. 5,524,133, issued Jun. 24, 1996, describes an X-ray analysis device for determining the mean atomic number of a material mass by locating a broad band X-ray source on one side of a testing station and on the other, a detector, comprising a target having X-ray detectors positioned adjacent thereto. One of the detectors is positioned and adapted to receive X-rays scattered by the detector target in a generally rearward direction and the other detector is positioned and adapted to detect forwardly propagating X-rays scattered off axis typically by more than thirty degrees, due to so-called "Compton scatter." Each of the X-ray detectors provides signals proportional to the number of X-ray photons incident thereon. The apparatus further includes means responsive to the two detector outputs which form a ratio of the number of photons detected by the two detectors and forms a numerical value thereof. A look-up table containing mean atomic numbers for given numerical ratios for different materials is used, as is a means for determining from the look-up table the atomic number corresponding to the numerical ratio obtained from the outputs of the two detectors. The atomic number is provided as an output signal.

U.S. Pat. No. 5,483,569, issued Jan. 9, 1996, describes an inspection system for inspecting objects with "penetrating radiation" having a conveyor with first and second portions which are separated by a gap. Illumination by this radiation is provided in a scanning plane which is located in the gap, and the system may be used for the inspection of thin objects. Additionally, the illumination may be arranged in the inspection of normal size objects, e.g., suitcases or cargo boxes, so that it does not include a ray which is perpendicular to any face of the object. Further, the relative orientation of the scanning plane and the faces of the object may be arranged so that the illumination does not include a ray which is parallel to any face of the object. A scanning configuration wherein the illumination does not include a ray which is perpendicular or parallel to any face of an object having parallel faces, for example, a rectangular solid, results in a display projection of the object which appears to be three dimensional.

U.S. Pat. No. 5,259,012, issued Nov. 2, 1993, describes a system which enables multiple locations within an object to be imaged without mechanical movement of the object. The object is interposed between a rotating X-ray source and a synchronized rotating detector. A focal plane within the object is imaged onto the detector so that a cross-sectional image of the object is produced. The X-ray source is produced by deflecting an electron beam onto a target anode. The target anode emits X-ray radiation where the electrons are incident upon the target. The electron beam is produced by an electron gun which includes X and Y deflection coils for deflecting the electron beam in the X and Y directions. Deflection voltage signals are applied to the X and Y deflection coils, and cause the X-ray source to rotate in a circular trace path. An additional DC voltage applied to the X or Y deflection coil will cause the circular path traced by the X-ray source to shift in the X or Y direction by a distance proportional to the magnitude of the DC voltage. This causes a different field of view, which is displaced in the X or Y direction from the previously imaged region, to be imaged. Changes in the radius of the X-ray source path result in a change in the Z level of the imaged focal plane.

U.S. Pat. No. 5,026,983, issued Jun. 25, 1991, describes an apparatus for examining food products for undesired ingredients by means of laser irradiation. A laser beam scans the food products according to a predetermined pattern. Variations in the intensity of the laser beam passing through the food products indicate the presence of undesired ingredients. This method is carried out by an apparatus which comprises two parabolic mirrors, a laser emitting a laser beam so as to originate from the focus of one of the mirrors and a detection means positioned in the focus of the other mirror. The food products are moved between the mirrors by conveyor belts.

U.S. Pat. No. 5,020,086, issued May 28, 1991, describes a situation where an object is scanned by an X-ray beam from a circular position on a target resulting from the electron beam being scanned in a circle by appropriate control signals from a beam controller and applied to the deflection coils of a microfocus X-ray tube. Tomosynthesis is accomplished by the well-known method of in-register combination of a series of digital X-ray images produced by X-ray beams emanating from different locations. This is achieved by positioning an X-ray source at multiple points on a circle around a central axis. This system eliminates some mechanical motion in that the detector does not have to rotate. However, practical limitations of pixel size and resolution tend to limit this system to inspection of items with small fields of view. Additionally, the system still requires an X, Y table to position the object under the field of view.

The above patents and co-pending applications are incorporated herein by reference.

The present invention defines a new and unique inspection apparatus which, in one embodiment, uses imaging technology (e.g., XCT scanning), in such a manner that effective cooling of the scanning devices is assured. Such cooling is accomplished for a number of scanning devices in a new and unique manner representing a significant improvement over cooling apparatus such as described above. It is believed that such an inspection apparatus would constitute a significant advancement in the art.

OBJECTS AND SUMMARY OF THE INVENTION

It is a primary object of the present invention to enhance the imaging inspection apparatus art.

It is another object of the invention to provide an imaging inspection apparatus which enables facile inspection of articles while assuring effective cooling of the heat-generating scanning devices used therein.

It is yet another object of the invention to provide such an imaging inspection apparatus in which such cooling is accomplished in a facile, expeditious manner without significant alterations to the apparatus structure.

According to one aspect of the invention, there is provided an imaging inspection apparatus for inspecting objects located within articles, the imaging inspection apparatus comprising a frame structure, a plurality of heat-generating imaging devices positioned on the frame and adapted for directing beams onto articles located substantially within the apparatus to thereby inspect the articles, and for providing output signals as a result of the inspecting. The apparatus further includes a processing and analysis assembly adapted for receiving the output signals from the imaging devices and for analyzing these output signals to identify objects within the articles and cooling structure for directing cooling fluid over the imaging devices to cool the devices during operation thereof.

BEST MODE FOR CARRYING OUT THE INVENTION

For a better understanding of the present invention, together with other and further objects, advantages and capabilities thereof, reference is made to the following disclosure and appended claims in connection with the above-described drawings. Like figure numbers will be used from FIG. to FIG. to identify like elements in these drawings.

Figure 1:
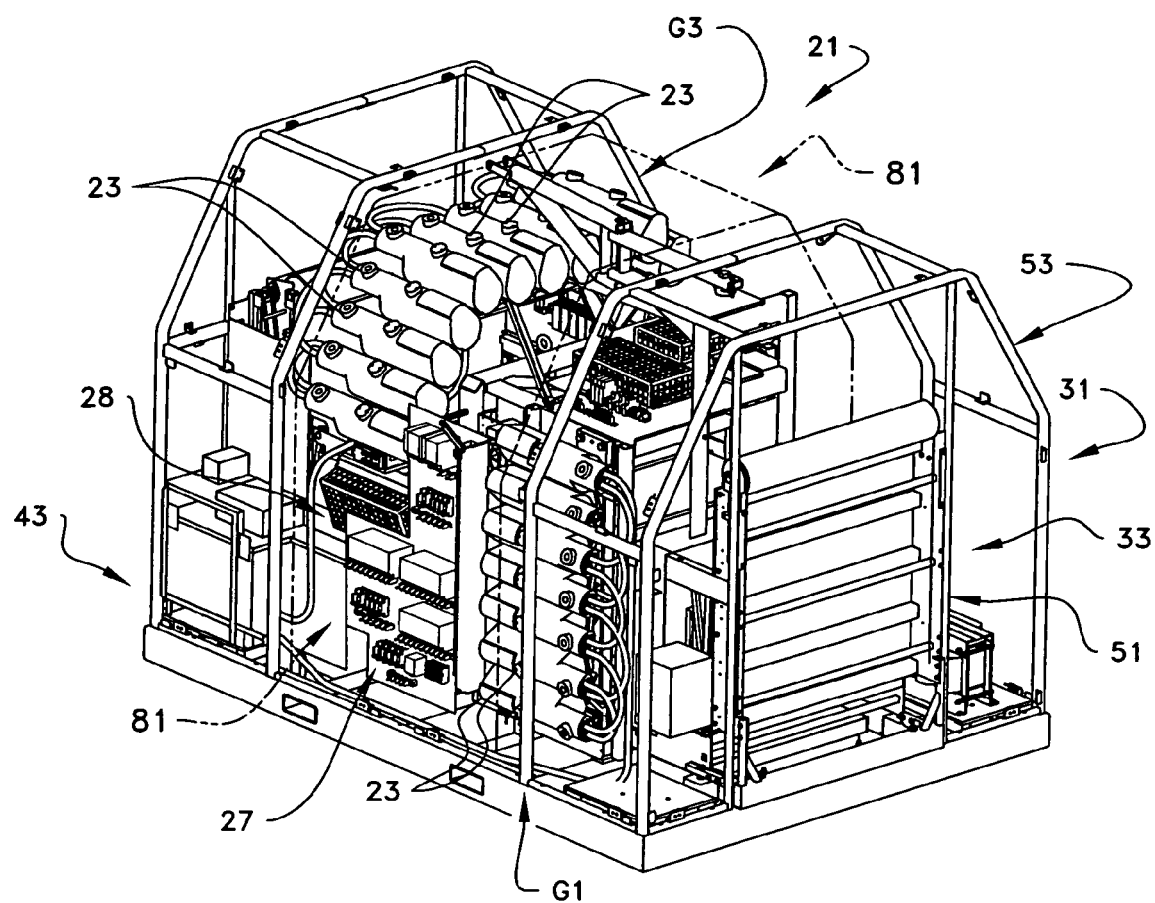
FIG. 1 is a front perspective view of an imaging inspection apparatus for inspecting objects located within articles, according to one embodiment of the invention.
Figure 2:
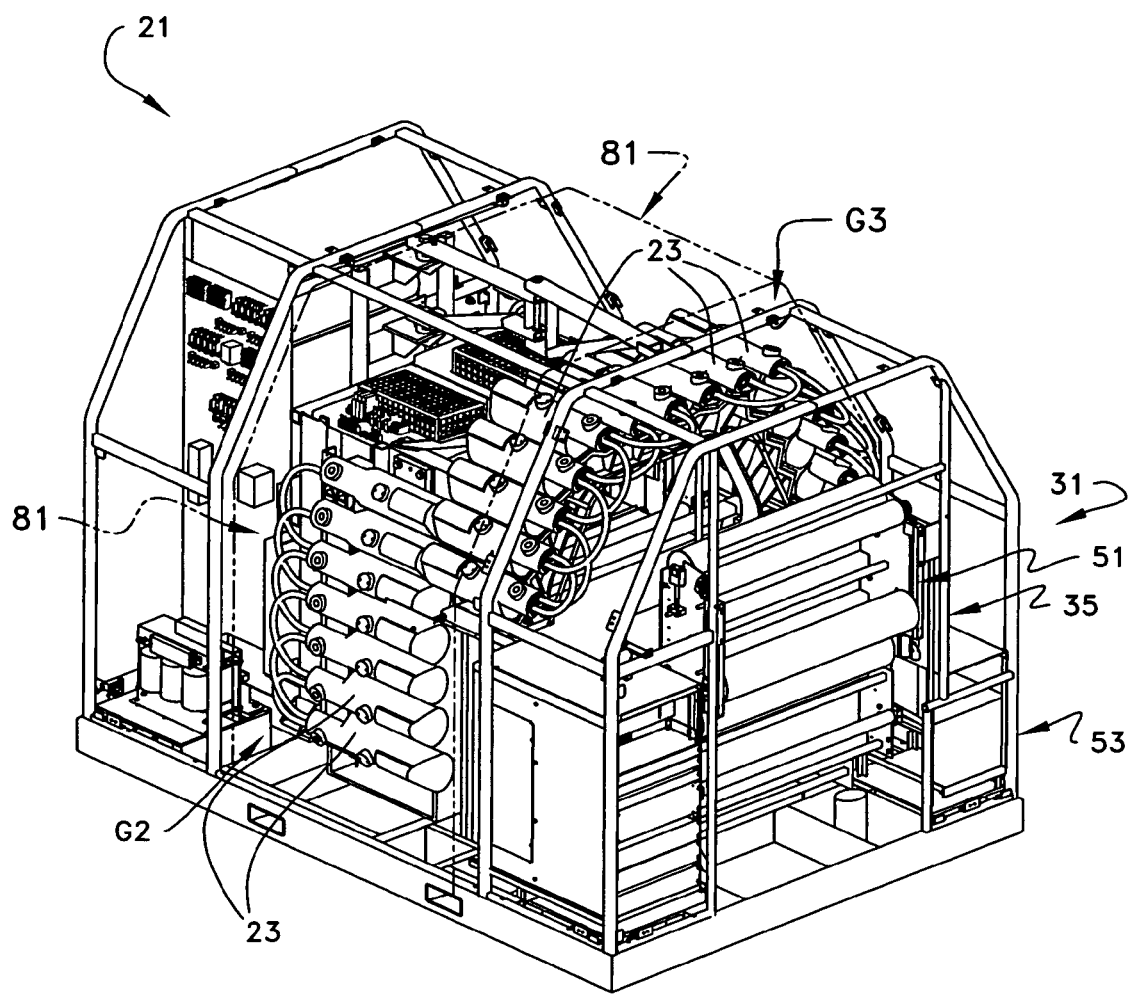
FIG. 2 is a rear perspective view of the imaging inspection apparatus for inspecting objects located within articles as shown in FIG. 1.
Figure 5:
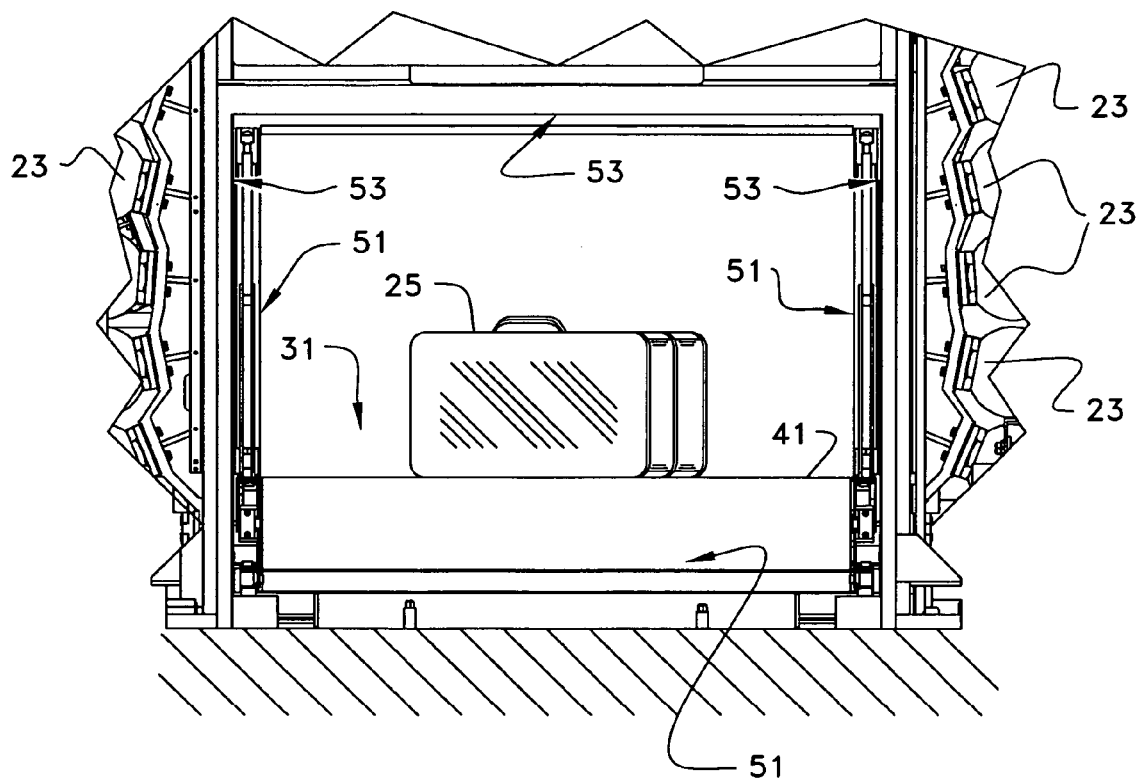
FIG. 5 is a partial end view of the apparatus of FIGS. 1 and 2, on an enlarged scale over the views of FIGS. 1-4.

One embodiment of an imaging inspection apparatus 21 of the invention is shown in FIGS. 1 and 2. As indicated, apparatus 21 is particularly designed for inspecting (and detecting) objects (not shown) which might be located within closed articles such as personal luggage of an airplane traveler. As such, the apparatus is ideally designed for placement and use within an airport or other transportation facility in which large numbers of such articles are received and transported. Apparatus 21 is adapted for inspecting and detecting concealed objects such as explosives, weapons, etc., including in solid and powder form. Further explanation of how apparatus operates is provided below. One example of such an article, this being a suitcase (luggage) 25, is shown in FIG. 5. Understandably, the apparatus inspects several such articles as these articles move therethrough, should the apparatus utilize a conveyor, as is preferred. The invention is not limited to apparatus using conveyors, however, as the teachings herein apply to any apparatus of this type in which heat-generating devices are utilized. Apparatus 21 includes a plurality of imaging inspection devices 23, which, in a preferred embodiment, are individual X-ray Computer Tomography (XRT) scanning devices. That is, each device is preferably an individual X-ray photon source, which is collimated to provide what may be referred to as a "fan beam." In one embodiment, these fan beams will each be collimated to a beam thickness of about 1 mm. over a distance of at least about 141 cm, with a divergence of about 0.7 milli-radians (or about 0.04 degree). Beams of such dimensions are preferred to substantially prevent background scatter and radiation leakage.

Devices 23 are arranged in three groupings G1, G2 and G3, with each grouping oriented in a particular orientation relative to the conveyor and thereby to the path of travel of the articles through the apparatus. Each grouping directs X-ray beams along a plane onto the articles, there thus being a total of three planes of beams (A, B and C, shown in FIGS. 3 and 4) which each article passes through while being inspected. In one embodiment, groupings G1 and G2 each include seven devices 23, and direct beams from opposite sides of the apparatus in a substantially horizontal manner, such that each article passing through the apparatus will receive beams toward the sides thereof. Grouping G3 includes fourteen devices 23 and directs beams from the top of the apparatus downwardly onto the articles, so that said articles will receive beams on the tops thereof. Each article is thus subject to pluralities of beams on at least three sides thereof. As the articles move through the three scan planes A, B and C, a number of lines of projection image data are formed for the scanned article in each scan plane. These lines of projection image data show the attenuation of the X-rays by the article and the object(s) (if any) therein. The density of an object scanned within the package can be calculated from the attenuation of the X-rays caused by the object.

In an arrangement of multiple X-ray devices 23 as shown, devices located near the center of a side of the image area will provide a higher intensity beam on a detector array (located opposite the devices for each grouping, one grouping of such detectors being represented by the numeral 27 in FIG. 1) because intensity decreases with the square of d, the distance of the device (source) from the detector element. Since the output of the detector elements of the detector array for all source locations should be equal, in the absence of an article such as a suitcase 25, it is necessary to progressively reduce the current for source locations toward the center of a side of the image for straight line source arrays. The same effect of maximizing the dynamic range of the system by substantially equalizing the output of the detectors in the detector array can also be achieved by curving the source array to progressively increase the distance between the sources and the detector arrays as the sources approach the center of the image area. This configuration provides substantially better coverage of the image area. Detectors used in each grouping 27 (three total, to accommodate the three groups of devices 23) and capable of performing in the manner defined herein are preferably of conventional construction and thus known in the art. Further description of this operation is provided in the above-mentioned U.S. Pat. No. 6,236,709. Each detector array 27 outputs five energy levels for each scan to provide multiple energies for the same set of data points, thus assuring the system is adapted for multi-spectral XCT re-construction. As mentioned or understood from the foregoing patents, systems of this type which use multiple filters to obtain multi-energy outputs from a detector are known. Alternatively, the detector systems can be constructed so that each detector provides an output signal to five comparators, each of which receives a different threshold voltage from a threshold source. The output of each comparator is a different energy level signal which represents the intensity of the spectral range above the comparator threshold input. The proportional decrease in the number of photons is a function of material chemical composition (i.e. atomic number).

The apparatus processing and analysis assembly 28 (FIG. 1) is preferably similar to the one used in U.S. Pat. No. 6,236,709, mentioned above. This assembly receives inputs from a sensor unit which includes the detector arrays 27. A pre-processing unit interfaces directly with the sensor units to provide buffering of the output data received from the sensor units. Timing is controlled by an input from a shaft encoder. Once the five level input has been received and stored by the preprocessing unit from each of the detector arrays for a single scan, an address generator in the preprocessing unit which is connected to a plurality of reconstruction signal processing boards generates a board address to determine which of the reconstruction signal processing boards will receive a current frame of data. Each reconstruction board, as defined in U.S. Pat. No. 6,236,709, contains several (e.g., up to sixteen) computer chips. These systems cooperate to provide calibration and normalization of the raw input data, and then conventional multi-spectral XCT reconstruction which includes algebraic reconstruction. During this reconstruction, each slice through the article being inspected is reconstructed at five different energies which are required to obtain the atomic number of an inspected (sensed) object. The algebraic reconstruction data is then sent to a detection and segmentation section of the apparatus which detects the atomic number and density of a scanned object located within one of the articles. For most materials, the linear X-ray attenuation coefficient mu is proportioned to the density. Thus the logarithm of the relative intensity of the X-ray beam is proportioned to the integral of the density of the material within the beam. The density and atomic number information is compared in a classification unit with information (criteria) within a reference table containing density and atomic number information for specific objects to be identified. This identification data and the reconstructed image data is then sent (preferably over a VME bus to a VME computer). The reconstructed XCT image data is displayed on the operator's console for review by the apparatus operator (and others, if desired). Processing of the data obtained from the scanning is preferably accomplished using the methodology (including the described ART algorithm, which employs a square grid of basis functions, centered at defined pixel locations all of the same form and diameter) described in U.S. Pat. No. 6,236,709, and further description is not believe necessary.

Figure 3:
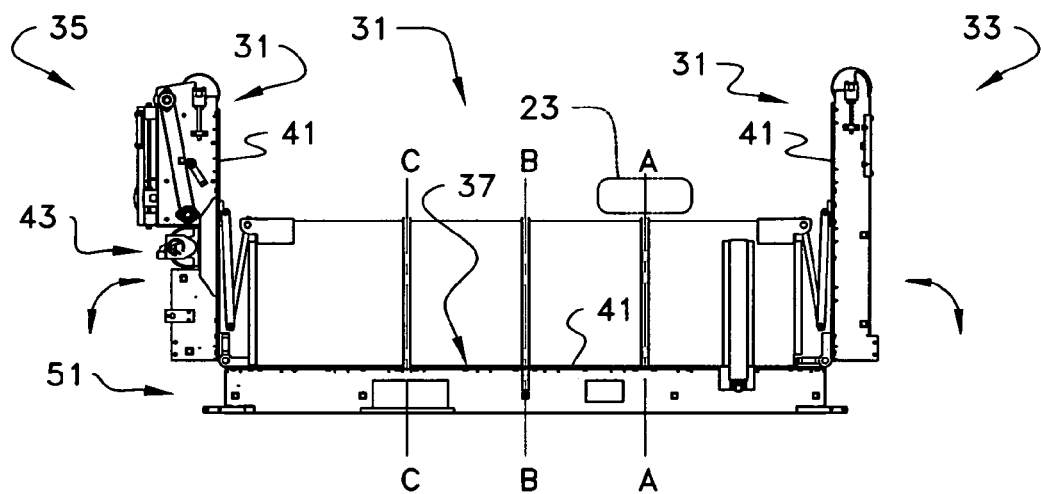
FIGS. 3 and 4 are side, elevational views, illustrating one embodiment of the invention in which a conveyor is used, the conveyor adapted for assuming both raised (closed) and lowered (opened, operating) positions, respectively, FIG. 4 being smaller in scale.
Figure 4:
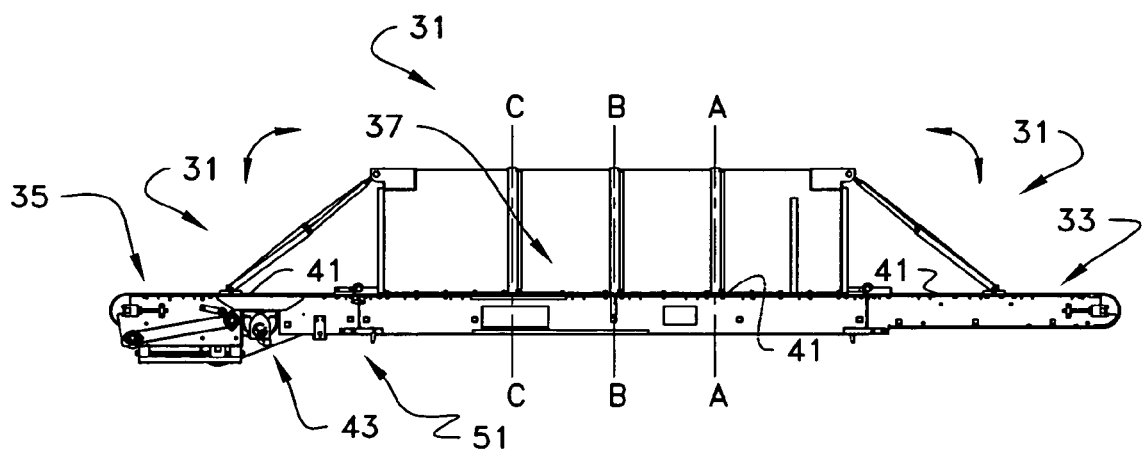

Apparatus 21 preferably utilizes a conveyor 31 of particular construction. That is, conveyor 31 includes three portions, a main body portion 37, and two opposing end portions 33 and 35. End portion 33 is also seen in FIG. 1, while opposite end portion 35 is also seen in FIG. 2, both of these end portions 31 and 33 in FIGS. 1 and 2 being in the withdrawn, closed position. As such, these ends are substantially vertically oriented relative to the main body portion 37 of conveyor 31. Also seen in FIGS. 3 and 4 are the three planes A, B and C, along which the groupings G1, G2 and G3 of devices 23 project their respective beams. Devices 23 are not shown in FIGS. 3 and 4 for ease of illustration, but it is understood from the above and FIGS. 1 and 2 that these devices would be positioned in a substantially planar grouping such that the planes A, B and C pass through substantially the center of a respective one of said groupings. One such device 23 is shown in phantom in FIG. 3 to illustrate this positioning orientation. Others are shown partly in FIG. 5, these devices forming part of groupings G1 and G2. The overhead devices of Grouping G3 are not shown in FIG. 5, but are clearly shown in the partial view of FIG. 6, including as mounted on the apparatus frame structure 53 (described in greater detail below).

Conveyor 31, similar to that defined in the aforementioned pending patent application Ser. No. 11/091,521, is shown in FIG. 4 as being in its substantially flat (or planar) operating position to accept and pass (move) articles such as suitcase 25 there-along. In one embodiment, articles are placed on portion 33 and conveyed (moved) to the body portion 37 and finally to the remaining end portion 35, from which it is then removed (or drops off) the conveyor. During such movement, the article passes through planes A, B and C, where individual groupings of scans are taken. As defined in Ser. No. 11/091,521, this movement occurs with substantially no adverse motion (e.g., excessive vibration) using the conveyor of this invention, such adverse motion, as explained above, possibly altering the readings of the scanned article. The apparatus of the co-pending application accomplishes this unique motion using a single belt 41 and a single drive (motor) 43, while spacedly positioning the conveyor having these two components thereon upon a support deck structure 51 (see especially FIG. 5) separate from the frame structure 53 that holds the remainder of the apparatus, including particularly devices 23 and the detectors of each grouping 27. This spacing is best seen in FIG. 5. There is thus no need to synchronize multiple belts, thereby also reducing the complexity of the invention over many prior such apparatus. Of further notation, drive motor 43 is located on end portion 35, even further spacing it from the main support structure for the apparatus remainder. In this arrangement, articles are conveyed along at a constant speed, the belt sliding over the spacedly positioned and rigid (in a preferred embodiment, the support deck structure is made of steel) support deck structure 51 which assure accurate planarity of the belt during such movement. The above capability is made possible while also providing a conveyor structure which can be significantly reduced in length by folding of the two end portions to the closed, non-operating position, to facilitate shipping and other handling, as well as servicing and inspection, of apparatus 21. Understandably, these capabilities represent significantly advantageous features over complex apparatus such as described in the above co-pending patent application. In one embodiment, the drive motor 43 is a one horsepower, 480 VAC, three phase, reversible electric motor with rubber lagging for enhanced belt traction. The rollers used to carry the belt are each of about 6.5 inch diameter and crowned for belt tracking. The belt itself possesses a width of one meter (39.3 inches). The belt speed may vary from about 1.22 to about 36.6 meters per minute (or about four to 120 feet per minute). The motor speed is controlled using a variable frequency drive.

Figure 6:
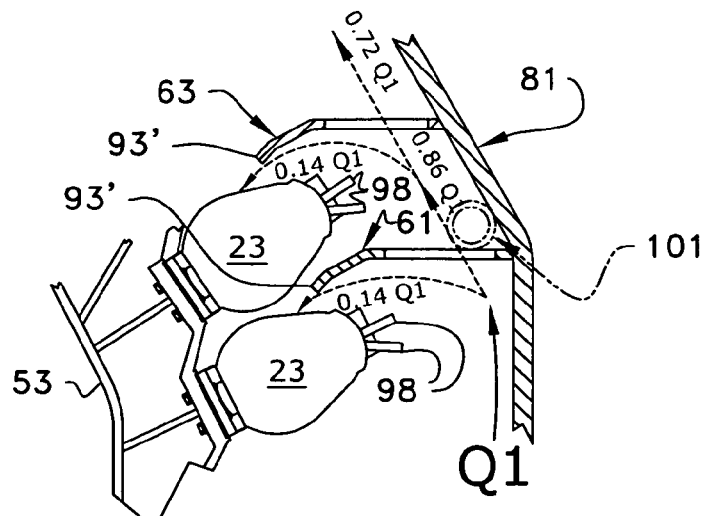
FIG. 6 is a partial view of two adjacent fluid deflectors positioned relative to two adjacent imaging devices according to one embodiment of the invention.

FIG. 6 illustrates two fluid deflectors 61 and 63 (also shown in FIG. 7) for use as part of the cooling structure of the invention, according to one embodiment thereof. Each deflector is designed for deflecting cooling fluid (e.g., air) provided from an air pump 66 (bottom right, FIG. 7) upwardly along one side of apparatus 21 onto a respective imaging device located adjacent thereto on part of frame structure 53. (This part of the frame structure is shown schematically in FIG. 7 for illustration purposes only and is not necessarily to the same detail shown elsewhere) Only two deflectors and devices are shown in FIG. 6 for ease of description and illustration purposes, with the entire bank (grouping G3) of fourteen such devices shown in FIG. 7. It is understood that similar deflector arrangements are used for the other groupings G1 and G2, each defined herein as preferably including seven imaging devices as part thereof. (The FIG. 7 embodiment shows two separate cooling structures, each including a fan (66 or 66') and six fluid deflectors, in addition to a "common" deflector (73) which one cooling structure "shares" with the sister cooling structure on the opposite side of the apparatus.) Each cooling structure as described herein is thus particularly adapted for cooling seven devices, but it is understood that this is not meant to limit the invention because modifications to the number are readily possible, depending on the total number of devices to be cooled. For example, it is possible to utilize a single fan for all fourteen devices as arranged in FIG. 7, with the last deflector (in this case, deflector 61') being solid, all others up to this last deflector having increasingly (proportional) smaller openings. Use of two fans and thus two "pairs" of deflector arrangements is also preferred to reduce flow resistance caused by a relatively large number of deflectors. Enhanced cooling is assured by ducting each of the fans 66 and 66' to an external environment, e.g., to outside air, away from the higher temperatures found within apparatus 21. Such ducting is not shown in FIG. 7 but is well understood to one of skill in the art.

Figure 7:
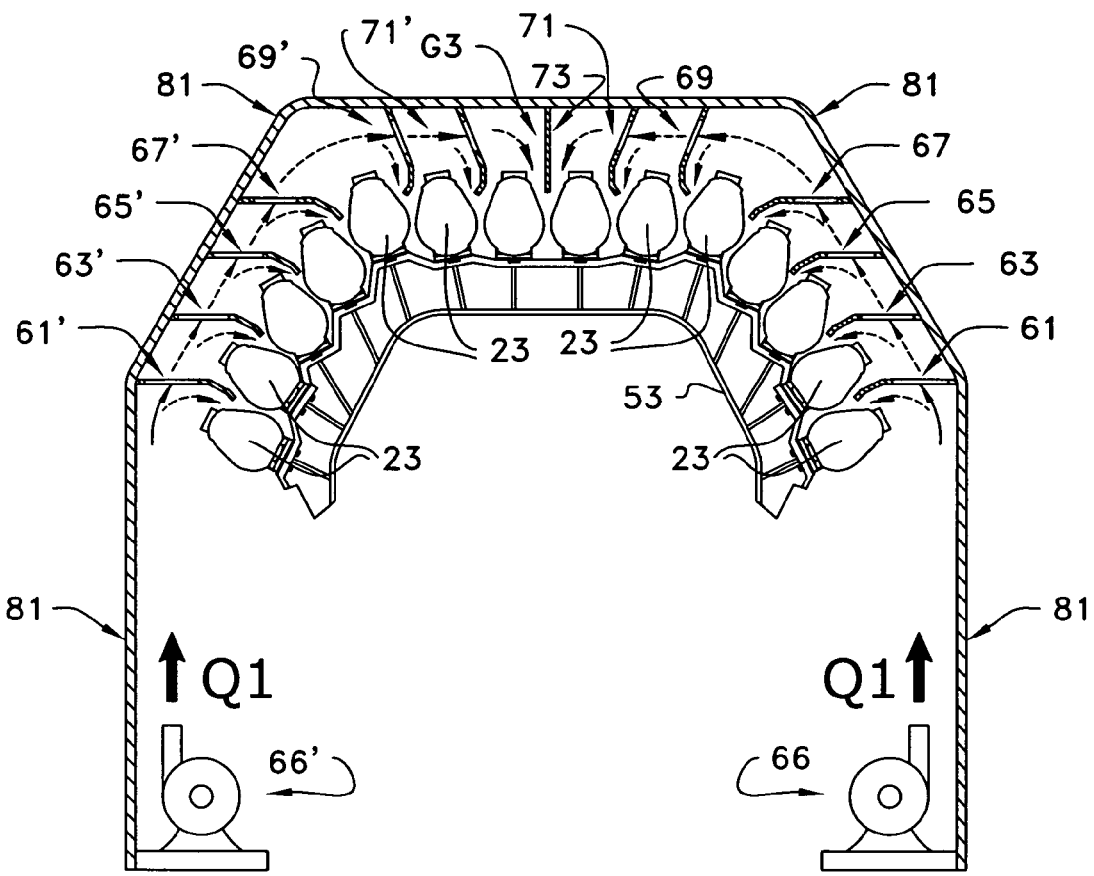
FIG. 7 is an elevational view depicting an arrangement of fluid deflectors for cooling one of the groupings of imaging devices for the apparatus shown in FIGS. 1 and 2, according to one embodiment of the invention.

Each deflector 61 and 63 is designed for deflecting a percentage of fluid from fan 66 onto a respective imaging device (i.e., deflector 61 deflects cooling fluid onto the first device 23 as shown by the dashed line 0.14 Q1). The fan 66 provides fluid in the direction shown by the arrow and the adjacent term Q1, this term meaning that the rate of flow at this point Oust prior to engaging the deflectors) is 100 percent. Significantly, each deflector is designed for deflecting a percentage of the fluid onto the adjacent, respective imaging device while simultaneously allowing a certain percentage of fluid to pass there-through. The proper percentage of air per imaging device is dependent on the number of devices needed cooling. In the example depicted in FIG. 7 (seven devices 23 for each cooling structure), approximately fourteen percent of the fluid is deflected by deflector 61, leaving a flow rate of eighty-six percent (0.86 Q1) to pass there-through on to the next deflector. Because seven devices are being cooled, the second deflector in line, deflector 63, also deflects fourteen percent of the fluid (0.14 Q1) and allows the remainder, 0.72 Q1 to pass. Significantly, each imaging devices will thus receive approximately fourteen percent of the fluid from the source, in this case, fan 66. Continued deflection of this percentage will occur by the remaining deflectors in the right-side cooling structure until all air is deflected onto all devices. The aforementioned "common" deflector 73 is preferably of solid construction and does not allow fluid passage, but instead deflecting all fluid impinging upon it downwardly onto the last remaining device 23, as seen in FIG. 7. A similar number of deflectors (61' through 71') are used for the left-side cooling structure which uses a separate cooling source, here also a fan (66'). The dashed lines in both FIGS. 6 and 7 represent the fluid direction for each side of apparatus 21, including both deflected and passed.

Figure 8:
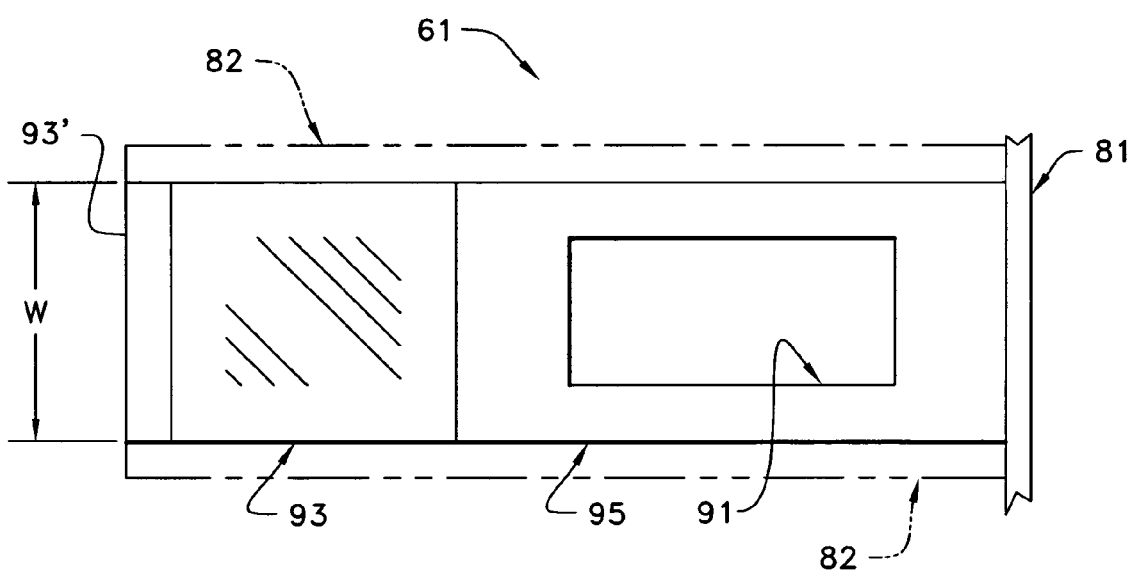
FIG. 8 is a much enlarged view (over the views in FIGS. 6 and 7) showing a plan view of a fluid deflector according to one embodiment of the invention.

To facilitate fluid passage, apparatus 21 includes a relatively solid panel structure 81 of substantially linear individual single panels which are located adjacent each of the three groupings G1, G2 and G3 of imaging devices. This panel structure is also shown in phantom in FIGS. 1 and 2. Five such panels are shown for the structure shown in FIG. 7, because of the relatively large number (fourteen) of imaging devices used for the grouping being cooled. A fewer number is possible for each of the seven device groupings G1 and G2. As seen in FIGS. 1 and 2, this panel structure is preferably large enough to cover all three groupings, although the invention is not so limited because individual panel arrangements may be used separately for each grouping. Although not shown, each flat panel also includes two side panel extensions which project from the panel alongside each deflector for a distance preferably at least as long as the deflector's length. (A singular, elongated side panel 82 (in phantom in FIG. 8) is preferably used along each of the two sides of all the deflectors in each grouping, if desired and if spacing allows.) Each such extension preferably abuts the side edge of the adjacent deflector to prohibit fluid side escape. Such extensions are well within the scope of one skilled in the art and further explanation is not necessary FIG. 8 illustrates one embodiment of a fluid deflector of the invention, this particular example being deflector 61 as shown in FIGS. 6 and 7. Deflector 61 includes an opening 91 therein, preferably of rectangular configuration as shown. Significantly, the openings in each of the deflectors in each group designed for one of the invention's cooling structures (in this case, deflectors 61 through 71), excluding common deflector 73, are proportionally smaller per deflector as the distance from the fluid source 66 increases. Such proportional reduction is opening size allows the desired percentages of fluid to pass through the deflectors in the manner taught herein, while assuring the appropriate percentage of fluid being directed onto each device. Thus, the opening in the last deflector 71 of the right-side cooling structure is smaller than all others, with the opening in the nearby adjacent deflector 69 being slightly larger, and so on, until the deflector with the largest opening, deflector 61 is reached. Similar proportionally smaller openings are used for the deflectors 61' through 71' on the left-side cooling structure, respectively, as is also the situation for the cooling structures designed for cooling the seven device groupings G1 and G2. As stated, deflector 73 is solid and includes no opening.

Cooling of each device is enhanced by the provision of a fluid turbulence promoter section 93, preferably also including an extension tip section 93', located at the end of the deflector body 95, each of these (section 93, tip section 93' and body 95) being of substantially linear (straight) configuration. (Tip sections 93' are also seen in FIGS. 6 and 7.) This is also not limiting of the invention as it is well within the scope of the invention to alter either or both of these shapes, e.g., one or both being curved. It is also within the scope of the invention to use openings 91 of a configuration other than rectangular. Annular, oval or other shapes are possible. It is even further possible to use a deflector shape other than substantially rectangular as shown in FIG. 8. For example, each deflector may be substantially oval. Cooling for the invention's cooling structures is even further enhanced by the provision of cooling pipes 101 (one shown in phantom in FIG. 6 for illustration purposes) which are positioned directly in contact with each deflector and through which a secondary cooling fluid is passed. Pipe 101 is shown only in FIG. 6 for illustration purposes and is not intended to be in any final position. It is fully understood that each pipe is not positioned so as to interfere with the passage of fluid through the deflector. It is even further understood that the cooling pipe may serve to assist in cooling the passing fluid as it passes adjacent thereto and thus in contact therewith as said fluid passes on to the next positioned deflector and imaging device combination. In a preferred embodiment, this secondary fluid is a liquid refrigerant of a type known in the art. A preferred coolant is sold by Thermo Electron Corporation, having a business address at 25 Nimble Hill Road, Newington, N.H., under the product designation "R404A" and is classified by this company as a CFC-free refrigerant. Cooling of this secondary fluid is possible using a heat exchanger, also known in the art. One preferred example is sold under the product designation "M 150" by the same Thermo Electron Corporation. This exchanger, which includes an internal pump for pumping the cooling refrigerant, has a cooling capacity at 20 degrees Celsius of greater than 17,000 BTU (British Thermal Units), and operates at 6045 watts. It is of compact design, uses a positive displacement pump and is UL (Underwriters Laboratory) compliant. This exchanger may be located in any convenient location within apparatus 21 and is thus not shown nor is it deemed necessary to illustrate its positioning as this is well within the abilities of one skilled in this art.

The width (W) of the deflector shown in FIG. 8 is of such a dimension so as to correspond to (and be positioned relative to) the corresponding highest temperature part of the adjacent device 23. It is thus not necessary for this width to be as long as the entire length of the device, for effective cooling to occur. In one embodiment of the invention, the deflector may possess a width of about nine inches while the corresponding imaging device 23 may possess a width of approximately twenty-four inches. Increasing the width of the deflector is readily possible, of course, including to the full length of the device 23, the invention not limited to the example mentioned herein.

Cooling of the individual imaging devices is also enhanced by the provision of heat-sinking fins 98 (shown in FIG. 6 only) which are positioned on the device bodies. In one embodiment, these fins 98 may be of aluminum or other well known heat-sinking metal, and may be either welded or attached mechanically or with suitable adhesive to the device body, as shown. More than two such fins are also possible.

Thus there has been shown and described an imaging inspection apparatus which assures effective cooling of the heat-generating imaging devices used therein so as to assure effective operation thereof. The cooling structures shown and defined herein are capable of effectively cooling the heat-generating imaging devices to thus enhance the operational life of each, while effectively cooling the ambient about apparatus 21.

While there have been shown and described what are at present the preferred embodiments of the invention, it will be obvious to those skilled in the art that various changes and modifications may be made therein without departing from the scope of the invention as defined by the appended claims.

What is claimed is:

1. An imaging inspection apparatus for inspecting objects located within articles, said imaging inspection apparatus comprising:
    a frame structure;
    a plurality of heat-generating imaging devices positioned on said frame structure and adapted for directing beams onto articles located substantially within said imaging inspection apparatus to thereby inspect said articles, and for providing output signals as a result of said inspecting;
    a processing and analysis assembly adapted for receiving said output signals from said plurality of heat-generating imaging devices and for analyzing said output signals to identify said objects within said articles; and
    cooling structure for directing cooling fluid over said plurality of heat-generating imaging devices to cool said devices during operation thereof, said cooling structure comprising a fan for directing said cooling fluid substantially in a first direction and a plurality of fluid deflectors spacedly positioned on said frame structure relative to said heat-generating imaging devices, selected ones of said fluid deflectors deflecting at least some of said cooling fluid from said fan onto selected ones of said heat-generating imaging devices.

2. The imaging inspection apparatus of claim 1 wherein said plurality of heat-generating imaging devices each comprise an XCT scanning device and said beams are X-rays.

3. The imaging inspection apparatus of claim 2 wherein the number of said XCT scanning devices is within the range of from about twenty to about forty devices.

4. The imaging inspection apparatus of claim 2 wherein said XCT scanning devices are positioned on said frame in at least three groupings, each grouping of said XCT scanning devices adapted for directing said X-rays along a different plane within said inspection location located substantially within said imaging inspection apparatus.

5. The imaging inspection apparatus of claim 4 wherein said XCT scanning devices of a first of said three groupings are positioned substantially vertically above said inspection location located substantially within said imaging inspection apparatus, and said XCT scanning devices of second and third groupings of said three groupings are positioned along opposite sides of said inspection location located substantially within said imaging inspection apparatus.

6. The imaging inspection apparatus of claim 5 wherein the number of said XCT scanning devices in said first grouping is fourteen and the number of said XCT scanning devices in each of said second and third groupings is seven.

7. The imaging inspection apparatus of claim 2 further including a plurality of X-ray detectors positioned on said frame and adapted for receiving said X-rays from selected ones of said XCT scanning devices as said X-rays pass through said articles.

8. The imaging inspection apparatus of claim 1 wherein selected ones of said fluid deflectors each include an opening therein for allowing passage of some of said cooling fluid there-through.

9. The imaging inspection apparatus of claim 8 wherein said fluid deflectors are positioned at different distances from said fan, said openings within said fluid deflectors being proportionately smaller as the distance from said fan increases such that said fluid deflectors nearest said fan allow a greater percentage of said cooling fluid to pass there-through than said fluid deflectors located at greater distances from said fan.

10. The imaging inspection apparatus of claim 1 wherein said cooling fluid is air.

11. The imaging inspection apparatus of claim 1 wherein selected ones of said fluid deflectors include a section thereof for promoting fluid turbulence of the fluid passing there-over.

12. The imaging inspection apparatus of claim 1 wherein said cooling structure further includes secondary cooling structure for cooling selected ones of said fluid deflectors.

13. The imaging inspection apparatus of claim 12 wherein said secondary cooling structure for cooling said selected ones of said fluid deflectors comprises a plurality of cooling pipes, selected ones of said cooling pipes being positioned in physical contact with a corresponding one of said heat deflectors.

14. The imaging inspection apparatus of claim 13 further including a pump for directing cooling fluid through said selected ones of said cooling pipes.

15. The imaging inspection apparatus of claim 14 wherein said cooling fluid directed through said selected ones of said cooling pipes is liquid refrigerant.

16. The imaging inspection apparatus of claim 1 wherein said apparatus further includes a conveyor for conveying said articles having said objects located therein along a path of travel through an inspection location located substantially within said imaging inspection apparatus.

17. The imaging inspection apparatus of claim 16 wherein said conveyor is not physically coupled to said frame structure and is also adapted for being folded to an orientation of a lesser length than that of said conveyor when said conveyor is conveying said articles along said path of travel.

18. The imaging inspection apparatus of claim 17 wherein said conveyor includes a support deck structure and a single belt, said single belt moving over said support deck structure when said conveyor conveys said articles along said path of travel.

19. The imaging inspection apparatus of claim 18 wherein said conveyor further includes a single drive for driving said single belt.

20. The imaging inspection apparatus of claim 17 wherein said conveyor comprises first, second and third portions, said first portion being a body portion and said second and third portions being end portions located at opposite ends of said body portion, each of said second and third end portions adapted for being moved to a position substantially perpendicular to said body portion.

* * * * *